US006299586B1

(12) United States Patent
Cao

(10) Patent No.: US 6,299,586 B1
(45) **Date of Patent: *Oct. 9, 2001**

(54) ACUPRESSURE POINT TREATING SYSTEM

(76) Inventor: Thanh D. Cao, 529 E. Washington Blvd., #6, Pasadena, CA (US) 91104

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/215,577

(22) Filed: Dec. 17, 1998

(51) Int. Cl.[7] ...................................... A61M 07/00

(52) U.S. Cl. .......................... 601/134; 600/587; 606/204

(58) Field of Search ................................ 601/133, 134, 601/135, 136, 137, 138, 140–142; 128/905, 907; 294/25; D24/171, 714, 215, 211; 600/301, 587, 557; 63/15; 607/75, 145, 146, 149, 150, 151; 606/204, 201; 401/8

(56) References Cited

U.S. PATENT DOCUMENTS

| | | | | |
|---|---|---|---|---|
| 681,054 | * | 8/1901 | Hawley | 401/8 |
| 990,158 | * | 4/1911 | Moses | 607/150 |
| 1,683,410 | * | 9/1928 | Rancourt | 601/161 |
| 1,761,356 | * | 6/1930 | McNamara | 401/8 |
| 2,103,083 | * | 12/1937 | Lynch | 601/139 |
| 2,112,184 | * | 3/1938 | Vogan | 601/139 |
| 2,121,701 | * | 6/1938 | Landers | 15/227 |
| 2,151,846 | * | 3/1939 | Greneker | 81/177.3 |
| 3,043,295 | * | 7/1962 | Ward | 601/139 |
| 3,505,700 | * | 4/1970 | Rodriguez | 401/8 |
| 3,623,481 | * | 11/1971 | Curran | 601/67 |
| 3,905,113 | * | 9/1975 | Jacob | 15/227 |
| 3,923,064 | * | 12/1975 | Leupold | D24/211 |
| 3,980,073 | * | 9/1976 | Shaw, IV | 600/547 |
| 4,034,982 | * | 7/1977 | Rupprecht et al. | 463/47.2 |
| 4,122,852 | * | 10/1978 | Knetsch et al. | 606/204 |
| 4,174,620 | * | 11/1979 | Russell | 63/1.12 |
| 4,177,698 | * | 12/1979 | Greneker | 30/298 |
| 4,183,359 | * | 1/1980 | Husbands | 606/43 |
| 4,267,838 | * | 5/1981 | McCall | 606/204 |
| 4,308,860 | * | 1/1982 | Sanders et al. | 601/137 |
| 4,358,118 | * | 11/1982 | Plapp | 463/7 |
| 5,070,563 | * | 12/1991 | Tervola | 7/167 |
| 5,137,507 | * | 8/1992 | Park | 600/13 |
| 5,314,260 | * | 5/1994 | Andersson | 401/7 |
| 5,519,292 | * | 5/1996 | Taylor et al. | 318/114 |
| 5,643,173 | * | 7/1997 | Welles | 600/26 |
| 5,766,131 | * | 6/1998 | Kondo et al. | 600/502 |
| 5,792,175 | * | 8/1998 | Yoo | 606/204 |
| 5,792,176 | * | 8/1998 | Chang | 606/204 |
| 5,797,854 | * | 8/1998 | Hedgecock | 600/554 |
| 5,885,018 | * | 3/1999 | Sato | 401/8 |
| 5,897,511 | * | 4/1999 | Kurita | 600/595 |
| 5,950,239 | * | 9/1999 | Lopez | 600/15 |

FOREIGN PATENT DOCUMENTS

| | | | | |
|---|---|---|---|---|
| 1461460 | * | 2/1989 | (SU) | 601/135 |

* cited by examiner

*Primary Examiner*—Justine R. Yu
(74) *Attorney, Agent, or Firm*—Christie, Parker & Hale, LLP

(57) ABSTRACT

An acupressure point treatment apparatus including an acupressure pointer including a pellet on a finger strap, a finger grounder including a grounding plate on a finger strap, and a Galvanic Skin Response (GSR) monitor electrically connected to the acupressure pointer and the finger grounder.

12 Claims, 1 Drawing Sheet

ACUPRESSURE POINT TREATING SYSTEM

FIELD OF THE INVENTION

This invention is a novel device for acupressure point therapy. More specifically, the apparatus is invented not only for treating but also for locating treatment points particularly on the four zones of extremities, i.e. ears, face, hands and feet.

BACKGROUND OF THE INVENTION

Pressure with pellets, on the ears, face, hands and feet, is just as effective as penetration with needles if treatment points are correctly located. A pellet can be non-metallic such as a grain or seed. A metal pellet, commonly known to practitioners as migraine pellet, acu-pellet or press pellet, is embedded in the center of a circular tape section, about 7.5 mm or 0.3" in diameter, to be applied adhesively on the skin. The pellet is usually plated with titanium, gold or silver, and has a blunt and polished circular contact surface, about 1.2 mm in diameter, to prevent skin penetration.

The use of such pellets is wasteful, because the pellet has to be disposed together with its used tape after each treatment. Furthermore, adhesive application is unnecessary and often causes adverse effect after a prolonged period of time.

Technically, acupuncture and acupressure points are located with a point locator which includes a low-current galvanometer, commonly known to acupuncturists as galvanic skin response (GSR) monitor or, to bio-feedback therapists, as skin conductance (SC) monitor, a search probe and a grounding pole. The GSR monitor is connected, by conducting wires, to the probe and pole. The grounding pole is held in patient's hand to establish ground contact, while practitioner holds the search probe, like a pen, and presses the probe tip at different locations on the patient's skin to detect a point. A treatment point is located in the region where electrical resistance of the skin is relatively lower than that of its surrounding. When the tip of the probe contacts the skin in that region, the lower resistance causes a surge of electric current through the GSR monitor. The current surge signifies a point location and appears on the monitor as a variation either in the display for readings or in the level of monitoring noises and/or illumination.

After locating the points, practitioners have to free their hand from the search probe to perform treatments on patient, either with needles for acupuncture, or pellets for acu-point pressure. The switching from point locating to treating performance is inconvenient and time consuming.

SUMMARY OF THE INVENTION

There are four particular zones of the points to be treated with the invented system; the four zones are on the ears, face, hands and feet.

Components of the acupressure point treating system of the present invention include an acupressure pointer, a finger grounder, connecting wires and a Galvanic Skin Response (GSR) monitor. The acupressure pointer can be used particularly by itself. When the pointer is connected by the connecting wire to the GSR monitor and operated together with a ground contactor, such as the finger grounder of the present invention or, alternatively, a common hand-held grounding pole, it forms the acupressure point treatment apparatus.

DETAILED DESCRIPTION OF THE INVENTION

Figure 1:
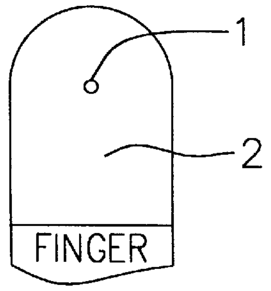
FIG. 1 is a bottom view of the acupressure pointer of the present invention.

FIG. 1, a bottom view of the acupressure pointer, shows pellet 1 coupled to a finger strap 2; the strap fits to a finger, like a guitar pick, to position the pellet in the vicinity of the finger tip.

Pellet 1, for the present invention, is metallic and made particularly of silver, since silver is highly conductive, and since silver coated pellets have proven to yield better therapeutic effect. The pellet can also be made of magnetized materials, such as iron and ceramic, for magnetic therapy.

Finger strap 2 is preferably insulated to prevent an electrical conduction between pellet 1 and the finger on which it is secured. The finger strap is therefore coated with a silicon layer or made of plastic. If the strap is plastic, the pellet is molded at its base in the plastic of the strap. If the strap is metal, the pellet is welded at its base to the metal of the strap. The tip of the pellet protrudes out of the strap to be applied on patient skin.

Figure 2:
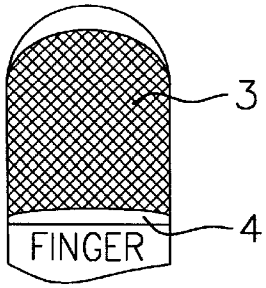
FIG. 2 is a bottom view of the finger grounder of the present invention.

FIG. 2, a bottom view of the finger grounder, shows grounding plate 3 coupled to finger strap 4; the strap fits to a finger, like a guitar pick, to position the grounding plate in the vicinity of the finger tip.

Grounding plate 3 is metallic. Its exposed surface is maximized to provide, as much as possible, ground contact when applied on patient's skin.

Finger strap 4 is preferably insulated to prevent an electrical conduction between grounding plate 3 and the finger on which it is secured. The finger strap is therefore coated with a silicon layer or made of plastic. If the strap is plastic, the grounding plate is molded partially in the plastic of the strap. If the strap is metal, surface of the grounding plate is the non-insulated surface part of the strap, or the grounding plate is welded to the metal of the strap. The grounding plate can also be coupled to the strap with epoxy cement.

Figure 3:
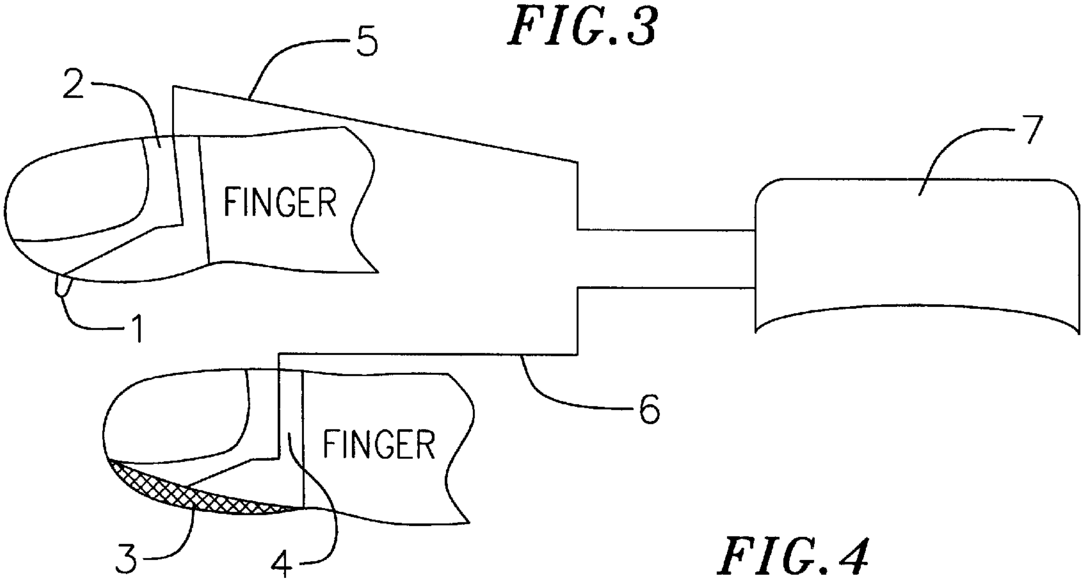
FIG. 3 is a side schematic view of the acupressure point treatment apparatus of the present invention.

FIG. 3 is a side schematic view showing an acupressure point treatment apparatus which includes an acupressure pointer and a finger grounder connected, respectively by conducting wire 5 and conducting wire 6, to GSR monitor 7. Wire 5 provides an electrical conduction between pellet 1 and monitor 7, and wire 6, between grounding plate 3 and monitor 7.

When pellet 1 is electrically connected to a GSR monitor, the tip of the pellet becomes equivalent to the tip of a common hand-held search probe; since the pellet of an acupressure pointer is secured to the finger tip by finger strap 2, practitioners no longer have to hold a search probe in their hand.

When grounding plate 3 is electrically connected to a GSR monitor, the exposed surface of the plate becomes equivalent to the exposed surface of a common hand-held grounding pole; since the grounding plate of a finger grounder is secured to the practitioner's finger tip by finger strap 4, patients no longer have to hold a grounding pole in their hand. Alternatively, a grounding pole can be used with the acupressure point treatment apparatus.

Figure 4:
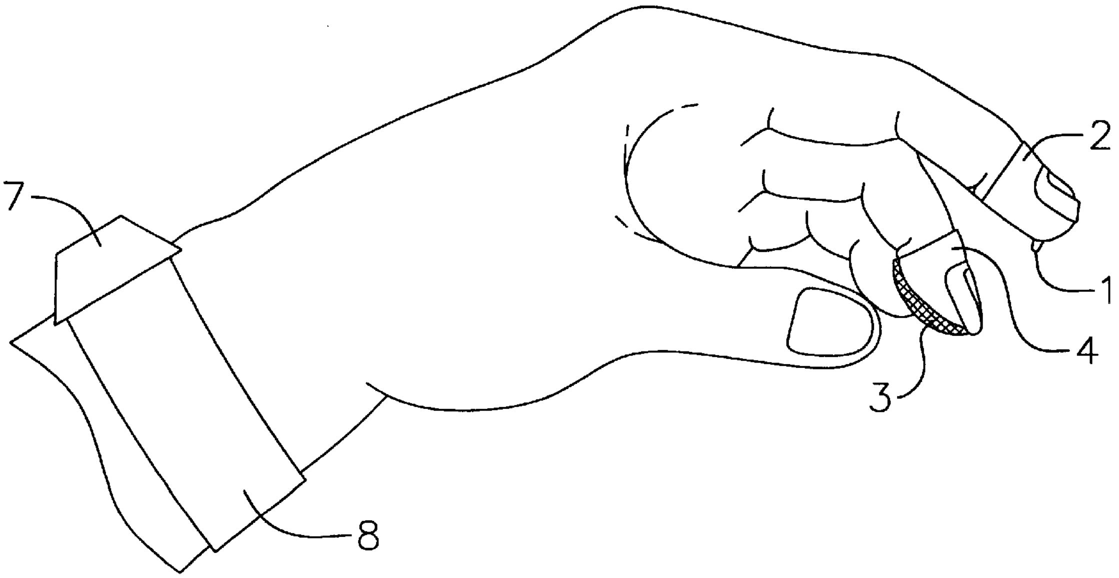
FIG. 4 is a schematic view of an alternative embodiment of the acupressure point treatment apparatus of the present invention.

FIG. 4 shows GSR monitor 7 with wrist strap 8; the strap secures monitor 7, like a watch, on the left wrist. The GSR monitor of the acupressure point treatment apparatus is connected to pellet 1 of the acupressure pointer, and to grounding plate 3 of the finger grounder. The conducting wires, 5 and 6, are not seen, because they are on the other side of the hand.

A GSR monitor is usually housed, together with other instruments of different functions, in a rather sizable case to be stationed on a table top. When isolated from the other instruments, a GSR monitor has been reduced in size to that of a fountain pen; one of such is currently marketed under the brand name of Pointer-Plus or Pointer-Pal. For the present invention, the case of GSR monitor 7 is formed, like a watch, and secured on a wrist by wrist strap 8 to provide freedom of hand movement for treatment performance.

If a treatment point is known, the acupressure pointer can be used without accessories. Practitioner simply applies the pellet of the pointer, secured at a finger tip, to generate the therapeutic effect of acu-point pressure on a patient. More than one holder can be used, on fingers of one or both hands, to treat more than one point simultaneously.

If the points have to be located before treatment, the acupressure pointer is connected, together with a ground contactor, to a GSR monitor. The acupressure pointer is used in place of a common search probe, and the tip of its pellet is equivalent to the tip of the search probe. Because application of the pellet remains at the same position, where the point is located and eventually to be treated, the procedure, including point detection and treatment, is conveniently simplified and precise.

Additional precision is provided by replacing the common hand-held grounding pole with a finger grounder. Because ground contact is established from applying the grounding plate of a finger grounder secured at practitioner's finger tip, not by patient's grip on a pole, the contact is more reliable under the practitioner's control, particularly when the patient cannot maintain sufficient firmness on the grip; more than one finger grounder can be used, on fingers of one or both hands, to increase ground contact. Alternatively, a grounding pole can be used with the acupressure point treatment apparatus.

Besides the convenience and precision for treatment and point detection, the acupressure point treatment apparatus provides the freedom of hand movements for treatment performance, because all components are secured to the practitioner's fingers and wrist.

Since its introduction to The United States after President Nixon's visit to China, acu-point treatment still remains, to communities of western medicines, intrigue with its claim for distant effect, e.g. stimulation of points on the ears relieves pain on the foot. This invention is a simple and convenient device to verify the effect of point stimulation which is not only distant, but also instantaneous. Furthermore, since a treatment with this invention does not involve skin penetration and requires only non-invasive pressure, it will help bring the reality of acu-point effect to better public awareness and acceptance.

What is claimed is:

1. An acupressure pointer comprising a pellet directly coupled to a finger tip strap whereby the strap includes a band extending around a finger and a rigid extension extending from the band and contoured to a shape of a ball of a finger tip, said pellet is located on the extension to position said pellet perpendicular to an axis of the finger adjacent the ball of the finger tip of an acupressurist for performing acupressure treatment, and a Galvanic Skin Response monitor electrically connected to the pellet and a ground contactor electrically connected to the Galvanic Skin Response monitor.

2. The acupressure pointer of claim 1 wherein the pellet is made of silver to enhance an effect of acupressure point therapy.

3. The acupressure pointer of claim 1 wherein the pellet is made of magnetized material to provide an effect of magnetic therapy.

4. The acupressure pointer of claim 1 wherein the finger tip strap includes a layer of insulation to prevent electrical conduction between the pellet and the finger tip of the acupressurist.

5. The acupressure pointer of claim 1 wherein the finger tip strap is made of electrically insulating material to prevent electrical conduction between the pellet and the finger tip of the acupressurist.

6. A finger grounder comprising an electrical grounding metal plate contoured to a shape of a ball of a finger tip and directly coupled to a finger tip strap whereby the strap positions said plate adjacent the ball of the finger tip of an acupressurist for performing acupressure treatment and a conducting wire connected to the grounding metal plate, and a Galvanic Skin Response monitor electrically connected to the grounding plate and a search probe electrically connected to the Galvanic Skin Response monitor.

7. The finger grounder of claim 6 wherein the finger tip strap includes a layer of insulation to prevent electrical conduction between the grounding plate and the finger tip of the acupressurist.

8. The finger grounder of claim 6 wherein the finger tip strap is made of electrically insulating material to prevent electrical conduction between the grounding plate and the finger tip of the acupressurist.

9. An acupressure point treatment apparatus comprising:

a Galvanic Skin Response monitor;

an acupressure pointer having a pellet electrically connected to the Galvanic Skin Response monitor and the pellet being coupled to a finger tip strap for positioning said pellet adjacent a finger tip of an acupressurist for performing acupressure treatment; and a ground contactor electrically connected to the Galvanic Skin Response monitor.

10. The acupressure point treatment apparatus of claim 9 wherein the ground contactor is a grounding pole.

11. The acupressure point treatment apparatus of claim 9 wherein the ground contactor is a finger grounder having a metal plate electrically connected to the Galvanic Skin Response monitor and the metal plate being coupled to a finger tip strap for securing the plate to the finger tip of the acupressurist.

12. The acupressure point treatment apparatus of claim 9 further comprising a wrist strap for securing the Galvanic Skin Response monitor to a wrist of the acupressurist.

* * * * *